United States Patent
Tsuneki et al.

(10) Patent No.: US 9,422,377 B2
(45) Date of Patent: Aug. 23, 2016

(54) PROCESS FOR PRODUCING ACROLEIN, ACRYLIC ACID AND DERIVATIVES THEREOF

(71) Applicant: Nippon Shokubai Co., Ltd., Osaka (JP)

(72) Inventors: Hideaki Tsuneki, Osaka (JP); Masanori Nonoguchi, Ibaraki (JP); Koji Nishi, Ibaraki (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 36 days.

(21) Appl. No.: 14/346,072

(22) PCT Filed: Sep. 25, 2012

(86) PCT No.: PCT/JP2012/074485
§ 371 (c)(1),
(2) Date: Mar. 20, 2014

(87) PCT Pub. No.: WO2013/047479
PCT Pub. Date: Apr. 4, 2013

(65) Prior Publication Data
US 2014/0303338 A1      Oct. 9, 2014

(30) Foreign Application Priority Data

Sep. 29, 2011   (JP) .................................. 2011-215651
Dec. 21, 2011   (JP) .................................. 2011-280519

(51) Int. Cl.
| | |
|---|---|
| C08F 20/10 | (2006.01) |
| C07C 45/52 | (2006.01) |
| C07C 45/78 | (2006.01) |
| C07C 51/235 | (2006.01) |
| C07C 45/86 | (2006.01) |
| C07C 51/25 | (2006.01) |
| C07C 67/05 | (2006.01) |
| C08F 20/06 | (2006.01) |

(52) U.S. Cl.
CPC .............. *C08F 20/10* (2013.01); *C07C 45/52* (2013.01); *C07C 45/78* (2013.01); *C07C 45/86* (2013.01); *C07C 51/235* (2013.01); *C07C 51/252* (2013.01); *C07C 67/05* (2013.01); *C08F 20/06* (2013.01)

(58) Field of Classification Search
CPC ....... C07C 45/52; C07C 45/78; C07C 45/86; C07C 51/235; C07C 51/252; C07C 67/05; C08F 20/06; C08F 20/10
See application file for complete search history.

(56) References Cited

U.S. PATENT DOCUMENTS

| | | | |
|---|---|---|---|
| 4,239,671 A * | 12/1980 | Fink et al. ................ | 524/813 |
| 5,770,021 A | 6/1998 | Hego et al. | |
| 7,612,230 B2 | 11/2009 | Shima et al. | |
| 7,951,978 B2 | 5/2011 | Arita et al. | |
| 8,178,719 B2 | 5/2012 | Shima et al. | |
| 8,212,070 B2 | 7/2012 | Dubois et al. | |
| 8,404,887 B2 | 3/2013 | Moriguchi et al. | |
| 8,609,893 B2 | 12/2013 | Devaux et al. | |
| 8,609,904 B2 | 12/2013 | Devaux et al. | |
| 2004/0159122 A1 | 8/2004 | Patel et al. | |
| 2004/0176641 A1 | 9/2004 | Tanimoto et al. | |
| 2007/0129570 A1 | 6/2007 | Shima et al. | |
| 2009/0068440 A1 | 3/2009 | Bub et al. | |
| 2009/0107175 A1 | 4/2009 | Patel et al. | |
| 2009/0113930 A1 | 5/2009 | Patel et al. | |
| 2009/0113931 A1 | 5/2009 | Patel et al. | |
| 2010/0063233 A1 | 3/2010 | Shima et al. | |
| 2010/0069583 A1 | 3/2010 | Kasuga et al. | |
| 2010/0105957 A1 | 4/2010 | Arita et al. | |
| 2010/0168471 A1 * | 7/2010 | Dubois .................... | 562/532 |
| 2010/0168472 A1 * | 7/2010 | Bogan et al. ............. | 562/532 |
| 2011/0237828 A1 | 9/2011 | Aoki et al. | |
| 2011/0257355 A1 | 10/2011 | Moriguchi et al. | |
| 2012/0060931 A1 | 3/2012 | Sakata et al. | |
| 2012/0302797 A1 | 11/2012 | Devaux et al. | |
| 2012/0330058 A1 | 12/2012 | Devaux et al. | |
| 2013/0017462 A1 | 1/2013 | Loevenbruck et al. | |
| 2013/0018161 A1 | 1/2013 | Ezawa et al. | |
| 2013/0053595 A1 | 2/2013 | Magatani et al. | |
| 2015/0005526 A1 | 1/2015 | Magatani et al. | |

FOREIGN PATENT DOCUMENTS

| | | | |
|---|---|---|---|
| EP | 1077206 | * | 2/2001 |
| EP | 2 186 790 | | 5/2010 |
| JP | 11-100343 | | 4/1999 |
| JP | 2004-255343 | | 9/2004 |
| JP | 2005-213225 | | 8/2005 |

(Continued)

OTHER PUBLICATIONS

Office Action issued Feb. 18, 2015 in corresponding Japanese Application No. 2011-215651, with English translation.

(Continued)

*Primary Examiner* — Paul A Zucker
*Assistant Examiner* — Mark Luderer
(74) *Attorney, Agent, or Firm* — Wenderoth, Lind & Ponack, L.L.P.

(57) ABSTRACT

A process for producing acrolein, comprising: a glycerin dehydration step of conducting dehydration reaction of glycerin to obtain an acrolein-containing gas; a partial-condensation step of cooling the acrolein-containing gas to condense a part of acrolein, water and a high-boiling substance contained in the acrolein-containing gas, thereby obtaining a purified gas and a condensate; and a separation step of separating the purified gas from the condensate; wherein a polymerization inhibitor is added to the acrolein-containing gas or the condensate in the partial-condensation step.

14 Claims, 4 Drawing Sheets

(56) References Cited

FOREIGN PATENT DOCUMENTS

| | | |
|---|---|---|
| JP | 2006-089531 | 4/2006 |
| JP | 2006-517541 | 7/2006 |
| JP | 2007-39348 | 2/2007 |
| JP | 2008-115103 | 5/2008 |
| JP | 2008-137949 | 6/2008 |
| JP | 2008-273885 | 11/2008 |
| JP | 2008-546660 | 12/2008 |
| JP | 2010-065001 | 3/2010 |
| JP | 2010-513422 | 4/2010 |
| JP | 2011-224537 | 11/2011 |
| WO | 2010/074177 | 7/2010 |
| WO | 2010/137454 | 12/2010 |
| WO | 2011/033689 | 3/2011 |
| WO | 2011/073552 | 6/2011 |
| WO | 2011/073553 | 6/2011 |
| WO | 2011/080447 | 7/2011 |

OTHER PUBLICATIONS

Office Action issued Mar. 24, 2015 in corresponding Japanese Application No. 2011-280519, with English translation.
Extended European Search Report issued Apr. 2, 2015 in corresponding European Application No. 12834615.2.
English Translation of Chinese Office Action dated Nov. 4, 2014 in correspondsing Chinese Application No. 201280047352.1.
International Search Report issued Dec. 4, 2012 in International (PCT) Application No. PCT/JP2012/074485.
Office Action issued Jul. 21, 2015 in corresponding Chinese Patent Application No. 201280047352.1 with English Translation.
Notice of Information Offer Form by Third Party issued Jul. 14, 2015 in corresponding Japanese Patent Application No. 2011-215651 with English Translation.
Notice of Reasons for Rejection issued Nov. 10, 2015 in corresponding Japanese Patent Application No. 2011-215651 with English translation.
Notice of Reasons for Rejection issued Nov. 24, 2015 in corresponding Japanese Patent Application No. 2011-280519 with English translation.
Office Action issued Mar. 2, 2016 in corresponding Chinese Patent Application No. 201280047352.1 with English translation.
Japanese Office Action issued Apr. 26, 2016, in corresponding Japanese Application No. 2011-215651, with English translation.
Decision of Refusal issued Jun. 7, 2016 in corresponding Japanese Patent Application No. 2011-280519 with English translation.

* cited by examiner

PROCESS FOR PRODUCING ACROLEIN, ACRYLIC ACID AND DERIVATIVES THEREOF

TECHNICAL FIELD

The present invention relates to a process for producing acrolein, a process for producing acrylic acid, and a process for producing acrylic acid derivatives such as a hydrophilic resin and an acrylic ester.

BACKGROUND ART

Biodiesel fuels produced from vegetable oils have drawn much attention as alternate fuels for fossil fuels and also in terms of low emission of carbon dioxide, and therefore, an increase in demand for them has been expected. Since the production of such biodiesel fuels is accompanied by formation of glycerin as a by-product, it is required to make effective utilization of glycerin. As an effective utilization of glycerin, a process for producing acrolein from glycerin of a raw material is known. For example, Patent Literatures 1 to 5 disclose processes for producing acrolein by dehydrating glycerin and processes for producing acrylic acid by oxidizing acrolein obtained by dehydration reaction of glycerin.

CITATION LIST

Patent Literature

Patent Literature 1
Japanese Unexamined Laid-open Patent Application Publication No. 2005-213225
Patent Literature 2
Japanese Unexamined Laid-open Patent Application Publication No. 2008-115103
Patent Literature 3
Japanese Unexamined Laid-open Patent Application Publication No. 2010-513422
Patent Literature 4
International Publication WO 2010/074177
Patent Literature 5
Japanese Unexamined Laid-open Patent Application Publication No. 2008-137949

SUMMARY OF INVENTION

Technical Problem

In producing acrolein by dehydration reaction of glycerin, since an acrolein-containing gas, resultant of the reaction, contains water and a high-boiling substance, it is preferred to refine the acrolein-containing gas. Especially, in the case where the acrolein-containing gas is used for a raw material of acrylic acid, when the acrolein-containing gas contains phenol or 1-hydroxyactone as the high-boiling substance, yield of acrylic acid decreases, that is not preferable.

As a refining method of the acrolein-containing gas, Patent Literatures 2 describes that distillation, partial-condensation, diffusion or the like can be employed; and the partial-condensation is preferably employed in respect that the acrolein-containing gas is able to be easily refined. In conducting refinement of the acrolein-containing gas by partial-condensation, it is preferred that cooling temperature of the acrolein-containing gas is decreased to condense a part of the gas, from a viewpoint of increasing removal ratio of water and the high-boiling substance from the acrolein-containing gas to enhance refining degree. However, it was found that problems such as blockage in equipments or pipes due to formation of deposit in a condensate easily occurred, as the refining degree of the acrolein-containing gas was enhanced.

The present invention has been achieved in view of the above circumstances, and the object of the present invention is to provide a process for producing acrolein, that enables highly refining the acrolein-containing gas obtained by dehydrating reaction of glycerin by employing partial-condensation and suppressing formation of deposit in the condensate, and a process for producing acrylic acid and its derivatives from acrolein obtained by the process for producing acrolein.

Solution to Problem

The present inventors have examined extensively and found that the deposit formed in the condensate, which was obtained when the acrolein-containing gas was partially-condensed, was an acrolein polymer. Thus, it has been cleared that, in refining the acrolein-containing gas by partial-condensation, enhancing refinement degree of the acrolein-containing gas causes accompaniment of acrolein in the obtained condensate, and acrolein contained in the condensate polymerizes to generate an acrolein polymer, that deposits in equipments or pipes. And, it has been also cleared that addition of a polymerization inhibitor to the acrolein-containing gas or the condensate in a partial-condensate step is effective for suppressing formation of the acrolein polymer.

That is, a process for producing acrolein of the present invention comprises: a glycerin dehydration step of conducting dehydration reaction of glycerin to obtain an acrolein-containing gas; a partial-condensation step of cooling the acrolein-containing gas to condense a part of acrolein, water and a high-boiling substance contained in the acrolein-containing gas, thereby obtaining a purified gas and a condensate; and a separation step of separating the purified gas from the condensate; wherein a polymerization inhibitor is added to the acrolein-containing gas or the condensate in the partial-condensation step. According to the process for producing acrolein of the present invention, formation of an acrolein polymer is suppressed, whereby it becomes possible to produce acrolein with high purity stably. In addition, by adding a polymerization inhibitor in the partial-condensation step, formation of an acrolein polymer is suppressed in a pipe as well as in a condenser, resulting in enabling stably operation of the condenser and the like for a long period.

It is preferred that the condensate forms single liquid phase. The condensate separates into two liquid phases when water content is low or acrolein content is high. In this case, even though the polymerization inhibitor is added to the condensate, polymerization of acrolein tends not to be efficiently suppressed in the condensate due to difference in concentration of the polymerization inhibitor between the two phases. Thus, when the condensate forms single liquid phase, formation of the acrolein polymer is effectively suppressed by adding a polymerization inhibitor to the condensate. For making the condensate form single liquid phase, it is preferred that a mass ratio of acrolein/(water+hydroxyacetone) in the condensate is 20/80 or less. Further, in the partial-condensation step, it is preferred that acrolein contained in the acrolein-containing gas does not condense as much as possible; and therefore, it is preferred that less than 10% of acrolein contained in the acrolein-containing gas condenses.

The present invention further provides a process for producing acrylic acid, comprising an acrolein oxidation step of conducting oxidation reaction of acrolein contained in the purified gas obtained by the above process for producing acrolein. When the purified gas obtained by the process for producing acrolein of the present invention is used as a raw material of acrylic acid, acrylic acid is able to be produced in high yield.

In the process for producing acrylic acid from glycerin via acrolein, it is preferred that: glycerin is introduced into a first reactor to conduct the dehydration reaction in the dehydration step; the acrolein-containing gas discharged from the first reactor is introduced into a condenser to be cooled at a pressure Pc lower than atmospheric pressure in the partial-condensation step; the purified gas discharged from the condenser is introduced into a second reactor to conduct the oxidation reaction of acrolein in the acrolein oxidation step; and the purified gas obtained by the partial-condensation step is introduced into the second reactor while acrolein contained in the purified gas remains in a gaseous state, wherein an inlet pressure of the second reactor is adjusted at a pressure Ps higher than the pressure Pc. When acrylic acid is produced from glycerin via acrolein in this manner, it becomes possible to efficiently produce acrylic acid while suppressing loss of acrolein due to polymerization of acrolein. For raising the pressure of the acrolein-containing gas, a pressure riser may be employed. Specifically, it is preferred that the pressure of the acrolein-containing gas is adjusted at the pressure Ps by introducing the purified gas discharged from the condenser into a pressure riser, followed by introducing an adjustment gas into the pressure riser or compressing in the pressure riser.

For suppressing condensation of acrolein in the purified gas when pressure of the purified gas is raised by the pressure rise, it is preferred that heating is combined with as follows. That is, it is preferred that: the inlet pressure of the second reactor is adjusted at the pressure Ps by introducing the purified gas discharged from the condenser into the pressure riser, followed by introducing the adjustment gas having a temperature higher than that of the purified gas introduced into the pressure riser, into the pressure riser; or the inlet pressure of the second reactor is adjusted at the pressure Ps by heating the purified gas discharged from the condenser, introducing it into the pressure riser and then compressing, or introducing the purified gas discharged from the condenser into the pressure riser, compressing and then heating.

For suppressing condensation of acrolein contained in the purified gas efficiently, the pressure Pc is preferably 1 kPa or higher and 90 kPa or lower. In addition, for conducting oxidation reaction of acrolein efficiently, the pressure Ps is preferably 110 kPa or higher and 300 kPa or lower.

The present invention further provides: a process for producing a hydrophilic resin comprising the step of polymerizing a monomeric component(s) including the acrylic acid obtained by the above process for producing acrylic acid; a process for producing an acrylic ester comprising the step of esterifying the acrylic acid; and a process for producing an acrylic ester resin, comprising the step of polymerizing a monomeric component(s) including the acrylic ester. As the hydrophilic resin, an absorbent resin is particularly preferred.

Advantageous Effects of Invention

According to the process for producing acrolein of the present invention, when the acrolein-containing gas obtained by dehydrating glycerin is refined by partial-condensation, formation of an acrolein polymer, whereby it becomes possible to produce acrolein with high purity stably. Acrolein obtained by the process for producing acrolein of the present invention is suitably used for a raw material of acrylic acid, and by using it as a raw material, it becomes possible to produce acrylic acid and its derivatives efficiently.

DESCRIPTION OF THE PREFERRED EMBODIMENTS

[Process for Producing Acrolein]

A process for producing acrolein of the present invention comprises: a glycerin dehydration step of conducting dehydration reaction of glycerin to obtain an acrolein-containing gas; a partial-condensation step of cooling the acrolein-containing gas to condense a part of acrolein, water and a high-boiling substance contained in the acrolein-containing gas, thereby obtaining a purified gas and a condensate; and a separation step of separating the purified gas from the condensate.

In the glycerin dehydration step, glycerin is dehydrated to obtain an acrolein-containing gas. The glycerin dehydration step may be performed by a conventionally-known method. Specifically, the dehydration reaction of glycerin is preferably conducted in the presence of a catalyst, thereby obtaining the acrolein-containing gas.

Glycerin used as a raw material is not particularly restricted, and glycerin derived from natural resources, such as glycerin obtained by hydrolysis reaction of a vegetable oil such as palm oil, palm kernel oil, coconut oil, soybean oil, rape seed oil, olive oil or sesame oil, or ester exchange reaction thereof with an alcohol; and glycerin obtained by hydrolysis reaction of an animal fat or oil such as fish oil, beef tallow, lard or whale oil, or ester exchange reaction thereof with alcohol; or glycerin chemically synthesized from ethylene, propylene, or the like can be used.

As a catalyst for dehydrating glycerin, that may be hereinafter referred as a "glycerin dehydration catalyst", a solid acid can be used, and examples of the solid acid include, for example, a crystalline metallosilicate, a metal oxide, a mineral acid, a clay mineral and a catalyst in which a mineral acid is supported on an inorganic carrier. Examples of the crystalline metallosilicate include compounds containing at least one kind of T atoms selected from the group consisting of Al, B, Fe, Ga and the like, and having a crystalline structure such as, for example, LTA, CHA, FER, MFI, MOR, BEA and MTW. Examples of the metal oxide include metal oxides such as $Al_2O_3$, $TiO_2$, $ZrO_2$, $SnO_2$ and $V_2O_5$, and complex oxides such as $SiO_2$—$Al_2O_3$, $SiO_2$—$TiO_2$, $TiO_2$—$WO_3$ and $WO_3$—$ZrO_2$. Examples of the clay mineral include bentonite, kaolin and montmorillonite. Examples of the mineral acid include sulfuric acid such as $MgSO_4$, $Al_2(SO_4)_3$ and $K_2SO_4$, and phosphoric acid such as $AlPO_4$ and $BPO_4$. Examples of the catalyst in which a mineral acid is supported on an inorganic carrier include a catalyst in which phosphoric acid, sulfuric acid or the like is supported on a carrier such as α-alumina, silica, zirconium oxide and titanium oxide. The crystalline metallosilicate, the metal oxide, the mineral acid and the clay mineral may be supported on a carrier.

As the glycerin dehydration catalyst, a crystalline metallosilicate or a mineral acid is preferably used; and by using such glycerin dehydration catalyst, the dehydration reaction of glycerin is tend to efficiently proceed even when a glycerin-containing gas, a raw material, contains relatively small amount of water. As the crystalline metallosilicate, HZSM-5, which contains Al as the T atom and has a MFI structure, is preferable. As the mineral acid, a phosphoric acid is preferable, and aluminum phosphate; boron phosphate; and rare-earth metal phosphates such as neodymium phosphate, yttrium phosphate and cerium phosphate are more preferable. Specifically, when aluminum phosphate; boron phosphate; or a rare-earth metal phosphate such as neodymium phosphate, yttrium phosphate or cerium phosphate is used as the catalyst, the reaction is able to efficiently proceed even in a condition where only a small amount of water (steam) is contained in the raw material.

It is preferred that the glycerin dehydration catalyst is placed in a reactor and glycerin is introduced into the reactor to be brought into contact with the glycerin dehydration catalyst, thereby conducting the glycerin dehydration reaction. As the reactor, a fixed-bed reactor, a fluidized-bed reactor, a moving-bed reactor or the like can be employed. In respect of suppressing physical damage of the catalyst such as abrasion and elongating catalyst lifetime, a fixed-bed reactor is preferably employed as the reactor. In the present invention, a reactor for conducting the glycerin dehydration reaction may be referred to as a "first reactor".

The dehydration reaction of glycerin may be performed in a liquid phase or a gas phase; and in consideration of obtaining the acrolein-containing gas as a reaction product, the dehydration reaction of glycerin is preferably conducted in a gas phase. In this case, glycerin is preferably subjected to the reaction in a gaseous state, and thus, it is preferred that the glycerin-containing gas is brought into contact with the catalyst, thereby conducting the dehydration reaction of glycerin.

The glycerin-containing gas may be composed of a gas only containing glycerin or a gas containing glycerin and other components inactive to the glycerin dehydration reaction (e.g. steam, nitrogen gas, carbon dioxide and air). Glycerin concentration in the glycerin-containing gas is generally in the range of 0.1 mol % to 100 mol %, preferably 1 mol % of higher, and more preferably 5 mol % or higher for economically and efficiently production of acrolein.

The glycerin-containing gas preferably contains steam. When the glycerin-containing gas contains steam, the amount of a carrier gas can be reduced and it becomes easy to obtain acrolein in high yield by the dehydration reaction of glycerin. Therefore, in view of enhancing acrolein yield in the glycerin dehydration reaction, concentration of steam in the glycerin-containing gas is preferably 0.1 mol % or higher, and more preferably 1 mol % or higher. Meanwhile, excess amount of steam in the glycerin-containing gas results in increase in utility cost for heating or cooling; and therefore, concentration of steam in the glycerin-containing gas is preferably 99 mol % or lower, more preferably 95 mol % or lower, even more preferably 80 mol % or lower, and particularly preferably 70 mol % of lower. The above-described concentration of steam in the glycerin-containing gas is especially effective for the case where aluminum phosphate; boron phosphate; or a rare-earth metal phosphate such as neodymium phosphate, yttrium phosphate or cerium phosphate is used as the glycerin dehydration catalyst. The concentration of steam in the glycerin-containing gas is a value relative to sum concentration of components except the carrier gas.

In the gas-phase dehydration reaction of glycerin, if reaction temperature is too low or too high, yield of acrolein decreases; and therefore, the reaction temperature is generally in the range of 200° C. to 500° C., preferably in the range of 250° C. to 450° C., and more preferably in the range of 300° C. to 400° C. In the present invention, the "reaction temperature" means a preset temperature of a heat medium or the like which control temperature of the reactor.

Pressure of the glycerin-containing gas to be introduced into the first reactor, that is, an inlet pressure of the first reactor, is not particularly limited as long as it is in the range that glycerin is not condensed, and is generally in the range of 0.001 MPa to 1 MPa. However, the inlet pressure of the first reactor is preferably not higher than atmospheric pressure, and for example, preferably 80 kPa or lower, more preferably 70 kPa or lower, and even more preferably 65 kPa or lower. When the inlet pressure of the first reactor is adjusted not higher than atmospheric pressure, heating temperature for evaporating glycerin does not need to be excess high in introducing the glycerin-containing gas into the first reactor, resulting in reducing loss of glycerin due to decomposition, polymerization or the like of glycerin. The lower limit of the inlet pressure of the first reactor is preferably 1 kPa, more preferably 10 kPa, and even more preferably 20 kPa.

An outlet pressure of the first reactor is a value calculated by subtracting pressure loss in the first reactor from the inlet pressure of the first reactor, and preferably less than atmospheric pressure. Specifically, the outlet pressure of the first reactor is preferably 80 kPa or lower, more preferably 70 kPa or lower, even more preferably 65 kPa or lower, and preferably 1 kPa or higher, more preferably 10 kPa or higher, even more preferably 20 kPa or higher. When the outlet pressure of the first reactor is 80 kPa or lower, it becomes easy to lower the temperature of the acrolein-containing gas while suppressing liquefaction (condensation) of acrolein as much as possible, thereby enabling suppression of acrolein polymerization. When the outlet pressure of the first reactor is 1 kPa or higher, an apparatus for achieving reduced-pressure condition does not have excessive specifications, resulting in decrease in equipment cost.

Partial pressure of glycerin contained in the glycerin-containing gas to be introduced into the first reactor is preferably 30 kPa or lower, more preferably 25 kPa or lower, even more preferably 20 kPa or lower, and particularly preferably 15 kPa or lower. By adjusting the partial pressure of glycerin is 30 kPa or lower, it becomes easy that yield of acrolein in the glycerin dehydration reaction is enhanced and deposition of carbonaceous matters onto the catalyst is suppressed. It is preferable that the partial pressure of glycerin is lower, however, from the viewpoint of industrial production, the lower limit of the partial pressure of glycerin is preferably 0.01 kPa, more preferably 1 kPa, and even more preferably 2 kPa.

In the case where a fixed-bed reactor is used as the first reactor, space velocity of the glycerin-containing gas introduced into the fixed-bed reactor is preferably 50 $hr^{-1}$ or more, and preferably 20000 $hr^{-1}$ or less, more preferably 10000 $h^{-1}$ or less, and even more preferably 4000 $h^{-1}$ or less. By adjusting the space velocity of the reaction gas in this manner, acrolein is able to be produced economically and efficiently. The space velocity is calculated by dividing volume of the reaction gas introduced into the fixed-bed reactor per unit time by volume of the catalyst filled in the fixed-bed reactor.

The acrolein-containing gas obtained by dehydration reaction of glycerin essentially contains acrolein and water (steam). In addition, the acrolein-containing gas possibly contains propionaldehyde, phenol, 1-hydroxyacetone, allyl alcohol and others as by-products. In the case where the acrolein-containing gas is used as a raw material of acrylic acid, phenol and/or 1-hydroxyactone is preferably removed from the acrolein-containing gas among these by-products. This is because yield of acrolein decreases in producing acrylic acid from the acrolein-containing gas when the acrolein-containing gas contains phenol and/or 1-hydroxyacetone in large amount. Thus, in the process for producing acrolein of the present invention, a partial-condensation step and a separation step are provided in order to remove high-boiling substances such as phenol and 1-hydroxyacetone as well as water to enhance content of acrolein in the acrolein-containing gas.

In the partial-condensation step, the acrolein-containing gas is cooled to condense water and a high-boiling substance contained in the acrolein-containing gas. The high-boiling substance includes phenol, 1-hydroxyaceton and others; and since boiling points under atmospheric pressure of acrolein, phenol and 1-hydroxyacetone are respectively about 53° C., about 182° C. and about 146° C., high-boiling substances such as phenol and 1-hydroxyactone is able to be preferentially removed from the acrolein-containing gas by cooling the acrolein-containing gas.

The high-boiling substance is not particularly limited as long as it is a substance which has a boiling point higher than that of acrolein, however, water is excluded from the high-boiling substance. Examples of the high-boiling substance include phenol, 1-hydroxyacetone, allyl alcohol, acetal, glycerin polycondensation and others. Preferably, the high-boiling substance includes phenol and/or 1-hydroxyacetone, and phenol and/or 1-hydroxyacetone condenses in the partial-condensation step.

By cooling the acrolein-containing gas, a condensate and a purified gas are obtained. Water and the high-boiling substance contained in the acrolein-containing gas condense to form the condensate. Further, in the producing process of the present invention, the acrolein-containing gas is cooled at relatively low temperature to improve performance of removing water and the high-boiling substance from the acrolein-containing gas; and as a result, a part of acrolein contained in the acrolein-containing gas also condenses to constitute a part of the condensate. Thus, according to the process for producing acrolein of the present invention, water and the high-boiling substance are highly removed from the acrolein-containing gas, whereby the purified gas contains acrolein in high purity is obtained. The purified gas corresponds to a gas component of which the condensate is removed from the acrolein-containing gas.

A method of cooling the acrolein-containing gas is not particularly restricted, and the acrolein-containing gas may be introduced into a condenser to be cooled. As the condenser, a heat exchanger is preferably employed.

In the case where a heat exchanger is used as the condenser, it is preferred that the heat exchanger is provided with a heat-transfer surface and the acrolein-containing gas is cooled by the heat-transfer surface. As the heat exchanger having the heat-transfer surface, an apparatus used as a heat exchanger which exchanges heat between a condensable gas and a liquid is preferably employed. For example, a plate-type heat exchanger comprising a single plate or a plurality of plates stacked at intervals, wherein heat is exchanged between one side and the other side of the each plate; a multitubular (shell-and-tube) heat exchanger comprising a plurality of tubes in a vessel, wherein heat is exchanged between the interiors and exteriors of the tubes; a double-pipe heat exchanger comprising an outer pipe and an inner pipe disposed in the outer pipe, wherein heat is exchanged between the interior and exterior of the inner pipe; a coil heat exchanger comprising one coil-shaped tube disposed in a vessel, wherein heat is exchanged between the interior and exterior of the tube; a spiral plate exchanger comprising a center tube whose cross-section is divided into two parts and two heat exchanger plates winding the center tube in whorl, whereby two whorl-like paths are formed; or the like may be employed.

In the partial-condensation step, cooling temperature of the acrolein-containing gas may be appropriately determined in the range lower than the dew point of steam contained in the acrolein-containing gas, in consideration of pressure in cooling, amount of heat exchanged in the heat exchanger and the like. For example, it is preferred that the lower limit of the cooling temperature of the acrolein-containing gas is appropriately determined in the range where less than 10% of acrolein in the acrolein-containing gas condenses in the partial-condensation step. Meanwhile, it is preferred that the upper limit of the cooling temperature of the acrolein-containing gas is appropriately determined in the range lower than the dew point of steam contained in the acrolein-containing gas introduced into the condenser. In view of enhancing the purity of acrolein in the purified gas to be obtained, the cooling temperature of the acrolein-containing gas (the lowest cooling temperature in the case where cooling is conducted in multiple steps to condense) is preferably set to be relatively low; and specifically, the cooling temperature is preferably 20° C. or higher, more preferably 40° C. or higher, and preferably 90° C. or lower, more preferably 85° C. or lower under the condition that operation pressure is atmospheric pressure.

In the partial-condensation step, operation pressure in cooling may be appropriately determined in consideration of pressures of the previous step and the next step; however, excess high or low temperature causes increase in cost concerning incidental equipments such as a compressor and a refrigerator, and thus, the operation pressure is generally in the range of 0.001 MPa to 1 MPa. In the partial-condensation step, the acrolein-containing gas is preferably cooled at a pressure lower than atmospheric pressure, and thereby, the acrolein-containing gas is able to be cooled at a lower temperature and it becomes easy to suppress polymerization of acrolein. In the partial-condensation step, though a part of acrolein may also condense, the purified gas preferably contains as much acrolein as possible. Therefore, less than 10% of acrolein contained in the acrolein-containing gas preferably condenses, more preferably less than 5% of that condenses, and even more preferably less than 3% of that condenses.

The operation pressure in cooling in the partial-condensation step, that is, pressure in the condenser, is not particularly limited, and may be a value calculated by subtracting pressure loss in a pipe and the condenser from the outlet pressure of the first reactor. Specifically, the pressure in the condenser is preferably 80 kPa or lower, more preferably 70 kPa or lower, even more preferably 65 kPa or lower, and preferably 1 kPa or higher, more preferably 10 kPa or higher, even more preferably 20 kPa or higher. When the pressure in the condenser is 80 kPa or lower, it becomes easy to lower the temperature of the acrolein-containing gas while suppressing condensation of acrolein as much as possible in the partial-condensation step. When the pressure in the condenser is 1 kPa or higher, an apparatus for achieving reduced-pressure condition does not have excessive specifications, resulting in decrease in equipment cost.

In the case where a plurality of condensers are provided as described below, acrolein-containing gas is preferably cooled at a pressure lower than atmospheric pressure in the every condensers. Operation conditions and the like in the each condenser are basically the same as those described above. However, in the case where the plurality of condensers are provided, cooling temperature of the acrolein-containing gas at a latter condenser (e.g. a second condenser) is preferably lower than that at a former condenser (e.g. a first condenser).

The purified gas and the condensate obtained by the partial-condensation step are separated into gas and liquid in the separation step. The purified gas obtained by gas-liquid separation in the separation step may be utilized as a raw material for producing acrylic acid or the like, may be condensed to be delivered as liquid purified acrolein, or may be subjected to further purification. Meanwhile, the condensate obtained by gas-liquid separation in the separation step is, for example, purged from the producing process as a waste liquid. The waste liquid may be appropriately treated by a known-method to recover water, that may be reused. As the apparatus for gas-liquid separation of the purified gas and the condensate, a known gas-liquid separator may be employed.

Here, the condensate contains acrolein, water and the high-boiling substance as described above, and acrolein is possibly polymerized in the condensate to deposit in an equipment or a pipe. As a result, there is concern that blockage in the equipment or the pipe occurs and the polymer deposited on the heat-transfer surface of the heat exchanger induces decrease in heat-exchange efficiency.

Therefore, in the process for producing acrolein in the present invention, a polymerization inhibitor is added to the acrolein-containing gas or the condensate in the partial-condensation step. Since acrolein easily polymerizes especially in solution, adding a polymerization inhibitor to the acrolein-containing gas or the condensate in the partial-condensation step enables suppression of forming an acrolein polymer in the condensate.

The polymerization inhibitor is preferably added at the point of formation of the condensate or just before that, and by adding the polymerization inhibitor at this timing, formation of the acrolein polymer is effectively suppressed in the condensate. Thus, the polymerization inhibitor is preferably added to the acrolein-containing gas or the condensate in the condenser, and more preferably added to the acrolein-containing gas in the condenser. In the case of using a heat exchanger as the condenser, it is preferred that the polymerization inhibitor is added to the acrolein-containing gas or the condensate in the heat exchanger.

The polymerization inhibitor is preferably added to the acrolein-containing gas or the condensate in a liquid state (including a solution state), and more preferably added to the acrolein-containing gas in the liquid state. Specifically, it is preferred that the polymerization inhibitor is added by showering the acrolein-containing gas with the polymerization inhibitor liquid in the condensate. When the polymerization inhibitor is added in this manner, the polymerization inhibitor is easily widely-spread among the condensate. In the case of showering the acrolein-containing gas with the polymerization inhibitor liquid in the heat exchanger, it is preferred that the polymerization inhibitor liquid is also poured onto the heat-transfer surface, whereby formation of the acrolein polymer is less likely to occur on the heat-transfer surface.

Conventionally-known polymerization inhibitors can be used as the polymerization inhibitor. Examples of the polymerization inhibitor include quinone compounds such as hydroquinone and methoquinone (p-methoxyphenol); phenothiazine compounds such as phenothiazine, bis-(α-methylbenzyl)phenothiazine, 3,7-dioctylphenothiazine and bis-(α-dimethylbenzyl)phenothiazine; N-oxyl compounds such as 2,2,6,6-tetramethylpiperidinooxyl, 4-hydroxy-2,2,6,6-tetramethylpiperidinooxyl and 4,4',4"-tris-(2,2,6,6-tetramethylpiperidinooxyl)phosphite; copper salt compounds such as copper dialkyl dithiocarbamate, copper acetate, copper naphthenate, copper acrylate, copper sulfate, copper nitrate and copper chloride; manganese salt compounds such manganese dialkyl dithiocarbamate, manganese diphenyl dithiocarbamate, manganese formate, manganese acetate, manganese octanoate, manganese naphtenate, manganese permanganate and manganese ethylenediamine tetra-acetate; nitroso compounds such as N-nitrosophenyl hydroxylamine or salts thereof, p-nitrosophenol and N-nitrosodiphenylamine or salts thereof; and the like. These polymerization inhibitors may be used alone or as a mixture of at least two of them. Among these polymerization inhibitors, quinine compound such as hydroquinone and methoquinone is preferably used.

An addition amount of the polymerization inhibitor may be appropriately determined in the range where the effect of inhibition of acrolein polymerization is produced in the condensate, and for example, the polymerization inhibitor is added preferably in the range of 100 ppm to 100000 ppm (more preferably 500 ppm to 50000 ppm and even more preferably 1000 ppm to 10000 ppm) relative to acrolein in the condensate.

The condensate formed in the partial-condensation step separates into two liquid phases of a water phase and an acrolein phase in condition of a low water content or a high acrolein content. The water phase contains water in high concentration and acrolein in relatively-low concentration. The acrolein phase contains acrolein in high concentration and water in relatively-low concentration. Generally, a polymerization inhibitor used for the purpose of preventing acrolein polymerization has high water solubility; and thus, when the polymerization inhibitor is added to the condensate of two liquid phases, the polymerization inhibitor mainly moves to the water phase. Therefore, in the case of adding the polymerization inhibitor to the condensate constituted two liquid phases, the effect of suppressing acrolein polymerization in the acrolein phase is lowered, and a large addition amount of the polymerization inhibitor is needed for suppressing formation of the acrolein polymer in the acrolein phase.

Accordingly, in the process for producing acrolein of the present invention, it is preferred that the condensate forms single liquid phase. When the condensate forms single liquid phase, formation of the acrolein polymer in the acrolein phase is effectively suppressed by adding the polymerization inhibitor to the condensate.

For making the condensate form single liquid phase, content of water in the condensate may be increased or content of acrolein in the condensate may be decreased. In addition, the condensate generally contains a part of 1-hydroxyacetone which is produced as a by-product of glycerin dehydration reaction at a ratio of up to about 20 mol % relative to acrolein, and when content of 1-hydroxyacetone in the condensate increases, mutual solubility of water and acrolein increases, whereby the condensate tends to form single liquid phase. Therefore, for making the condensate form single liquid phase, a mass ratio of acrolein/(water+ hydroxyacetone) in the condensate may be adjusted appropriately. Specifically, the mass ratio of acrolein/(water+ hydroxyacetone) in the condensate may be adjusted so that the condensate forms single liquid phase, depending on condensation temperature. For example, as the condition that the condensate maintains single liquid phase even when it is cooled to 20° C., the mass ratio of acrolein/(water+ hydroxyacetone) in the condensate is preferably 20/80 or less, more preferably 15/85 or less, and even more preferably 10/90 or less. Here, the mass ratio of acrolein/(water+ hydroxyacetone) in the condensate means a ratio of mass of acrolein to sum total of mass of water and mass of hydroxyacetone in the condensate. When the mass ratio of acrolein/(water+hydroxyacetone) in the condensate is adjusted in this manner, the condensate is easily made to form single liquid phase. The lower limit of the mass ratio of acrolein/(water+ hydroxyacetone) in the condensate is not particularly limited, and for example, it may be 1/99 or more.

For adjusting the mass ratio of acrolein/(water+hydroxyacetone) in the condensate, content of steam in the glycerin-containing gas may be adjusted in the glycerin dehydration step or cooling temperature in the partial-condensation step may be adjusted. As explained above, since in the glycerin dehydration reaction, glycerin is preferably accompanied with steam from a viewpoint of enhancing acrolein yield in the glycerin dehydration reaction, the mass ratio of acrolein/(water+hydroxyacetone) in the condensate is able to be lowered by increasing the content of steam in the glycerin-containing gas in the glycerin dehydration step. In addition, the mass ratio of acrolein/(water+hydroxyacetone) in the condensate is able to be lowered by adjusting the cooling temperature in the partial-condensation step to high temperature in the range lower than the boiling point of water.

The process for producing acrolein of the present invention may further comprise a second partial-condensation step and a second separation step, for enhancing purity of acrolein in the purified gas obtained by the separation step. In the second partial-condensation step, the purified gas obtained by the separation step is cooled to condense a part of acrolein, water and a high-boiling substance contained in the purified gas, thereby obtaining a second purified gas and a second condensate. In the second separation step, the second purified gas is separated from the second condensate.

The second partial-condensation step is basically conducted in the same manner as the above-described partial-condensation step. Therefore, regarding the second partial-condensation step, explanations which overlap with that about the partial-condensation step are omitted. In the case of conducting the second partial-condensation step, cooling temperature of the purified gas in the second partial-condensation step is preferably lower than that of the acrolein-containing gas in the partial-condensation step. Also in the second partial-condensation step, a polymerization inhibitor is added to the second purified gas or the second condensate. Since the polymerization inhibitor which was added in the former partial-condensation step is transferred to the condensate, the purified gas introduced into the second partial-condensation step does not practically contain a polymerization inhibitor. Therefore, in order to suppress formation of the acrolein polymer in the second condensate, addition of a polymerization inhibitor is also needed in the second partial-condensation step.

The second separation step is basically conducted in the same manner as the above-described separation step. Therefore, regarding the second separation step, explanations which overlap with that about the separation step are omitted. The second purified gas obtained by the second separation step contains acrolein with higher than the purified gas obtained by the former separation step. The second condensate obtained by gas-liquid separation in the second separation step may be purged from the producing process as a waste liquid, or may be returned to the former separation step for obtaining effect of reflux in order to enhance degree of refining.

The process for producing acrolein of the present invention may further comprise a third partial-condensation step and a third separation step, for enhancing purity of acrolein in the second purified gas obtained by the second separation step.

As explained above, according to the process for producing acrolein of the present invention, formation of the acrolein polymer in the condensate (including the second condensate) is suppressed, and hence, problems such as blockage due to formation of the acrolein polymer are less likely to occur and production of acrolein is facilitated. In addition, the obtained purified gas (including the second purified gas) contains acrolein in high concentration and has been removed a high-boiling substance, and hence, it is suitably used as, for example, a raw material for producing acrylic acid. Especially, when phenol and/or 1-hydroxyacetone as the high-boiling substance has been removed from the purified gas, using the purified gas as a raw material for producing acrylic acid enables obtaining acrylic acid in high yield by conducting gas-phase catalytic oxidation of the purified gas containing acrolein.

In the case where the purified gas (or the second purified gas) is used as a raw material for producing acrylic acid, a mass ratio of phenol/acrolein and a mass ratio of 1-hydroxyaceton/acrolein in the purified gas (or the second purified gas) are respectively preferably 0.020 or less, more preferably 0.010 or less, and even more preferably 0.005 or less. Meanwhile, when a removal amount of phenol and/or 1-hydroxyactone becomes large, it may be likely that loss of acrolein increases or purification of acrolein is complicated. Considering this matter, the mass ratio of phenol/acrolein and the mass ratio of 1-hydroxyaceton/acrolein in the purified gas (or the second purified gas) are respectively preferably $1\times10^{-9}$ or more, more preferably $1\times10^{-7}$ or more, and even more preferably $1\times10^{-5}$ or more.

Figure 1:
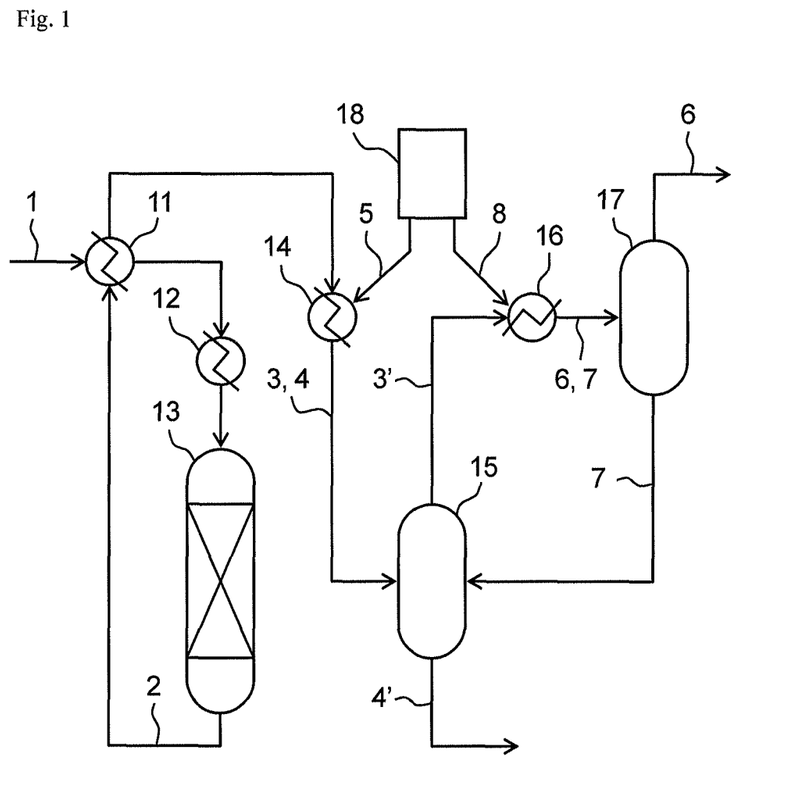
FIG. 1 shows an example of a process flow diagram used in the acrolein producing process of the present invention.

Next, an example of the process for producing acrolein of the present invention is explained, referring to FIG. 1. However, the process for producing acrolein of the present invention is not limited to the embodiment shown in the drawings.

A raw material 1 containing glycerin and water is allowed to pass through a first heat exchanger 11 and a second heat exchanger 12 to be heated to about 300° C. to 400° C., thereby giving a glycerin-containing gas, and the glycerin-containing gas is introduced into a fixed-bed reactor 13 filled with a glycerin dehydration catalyst. In the fixed-bed reactor 13, acrolein and water are produced by dehydration reaction of glycerin accompanied by formation of a high-boiling substance as a by-product.

The acrolein-containing gas 2 discharged from the fixed-bed reactor 13 is heat-exchanged with the raw material 1 in the first heat exchanger 11 to be cooled, and then introduced into the first condenser 14 to be cooled to, for example, about 85° C. As a result, in the first condenser 14, a part of acrolein, water and the high-boiling substance contained in the acrolein-containing gas 2 condense, thereby obtaining a condensate 4, while a purified gas 3, of which purity of acrolein is enhanced, is obtained. On this occasion, a polymerization inhibitor 5 is fed to the first condenser 14 from a polymerization inhibitor storage tank 18, whereby the polymerization inhibitor 5 is added to the acrolein-containing gas 2 or the condensate 4. As a result, polymerization of acrolein in the condensate 4 is suppressed, and troubles such as blockage in the first condenser 14, pipes thereafter or a first gas-liquid separator 15, due to deposition of an acrolein polymer, are less likely to happen.

The purified gas 3 and the condensate 4 which are discharged from the first condenser 14 and a second condensate 7 which is separated by a second gas-liquid separator 17 described below are introduced into the first gas-liquid separator 15 to be separated into a purified gas 3' and a condensate 4'. The condensate 4' is discharged from the bottom of the first gas-liquid separator 15 as a waste liquid. The purified gas 3' is introduced into a second condenser 16, whereby purity of acrolein is further enhanced.

The purified gas 3' introduced into the second condenser 16 is cooled to, for example, about 60° C.; and as a result, in the second condenser 16, a part of acrolein, water and the high-boiling substance contained in the purified gas 3' condense, thereby obtaining the second condensate 7, while a second purified gas 6, of which purity of acrolein is further enhanced, is obtained. On this occasion, a polymerization inhibitor 8 is fed to the second condenser 16 from the polymerization inhibitor storage tank 18, whereby the polymerization inhibitor 8 is added to the purified gas 3' or the second condensate 7. As a result, polymerization of acrolein in the second condensate 7 is suppressed, and troubles such as blockage in the second condenser 16, pipes thereafter or the second gas-liquid separator 17, due to deposition of an acrolein polymer, are less likely to happen.

The second purified gas 6 and the second condensate 7 which are discharged from the second condenser 16 are introduced into the second gas-liquid separator 17, whereby the second purified gas 6 is separated from the second condensate 7. The second condensate 7 is discharged from the bottom of the second gas-liquid separator 17, returned to the first gas-liquid separator 15, and further separated in the first gas-liquid separator 15 to be discharged therefrom as the condensate 4', a waste liquid. The second purified gas 6 is utilized for a raw material of acrylic acid, for example.

[Process for Producing Acrylic Acid]

Next, a process for producing acrylic acid of the present invention is explained. A process for producing acrylic acid of the present invention comprises an acrolein oxidation step of conducting oxidation reaction of acrolein contained in the purified gas (including the second purified gas) obtained by the process for producing acrolein of the present invention. In the process for producing acrolein of the present invention, the purified gas (or the second purified gas) from which phenol and/or 1-hydroxyacetone as a high-boiling substance has been highly removed is obtained; and hence, by conducting gas-phase catalytic oxidation of the purified gas, acrylic acid is able to be obtained in high yield.

The acrolein oxidation step may be performed by a conventionally-known method. Production of acrylic acid is preferably conducted by gas-phase catalytic oxidation of acrolein in the purified gas (or the second purified gas) in the presence of an acrolein oxidation catalyst. That is, it is preferred that the purified gas is introduced into a second reactor filled with an acrolein oxidation catalyst and acrolein contained in the purified gas is oxidized to obtain an acrylic acid-containing gas.

In the process for producing acrylic acid from glycerin via acrolein, it is important to suppress polymerization of acrolein for enhancing yield of acrylic acid, and therefore, it is preferred that temperature of the acrolein-containing gas or the purified gas is lowered while securing a ratio of acrolein remained in a gaseous state. Thus, it is preferred that the outlet pressure of the first reactor or the pressure in the condenser is adjusted lower than atmospheric pressure as described above, whereby liquefaction temperature of acrolein falls relative to that under atmospheric pressure, and it becomes possible to lower the temperature of the acrolein-containing gas or the purified gas while suppressing liquefaction (condensation) of acrolein as much as possible.

It is preferred that the purified gas discharged from the condenser is subjected to the acrolein oxidation step while acrolein remains in a gaseous state. In this case, at least a part of acrolein contained in the purified gas needs to remain in a gaseous state. When the purified gas is subjected to the acrolein oxidation step while the acrolein remains in a gaseous state, it becomes possible to produce acrylic acid in high yield while suppressing loss of acrolein due to acrolein polymerization. In addition, as compared to the case where acrolein prepared by dehydration reaction of glycerin is once condensed to be collected as an acrolein-containing liquid, and then the acrolein-containing liquid is heated to give an acrolein gas, that is subjected to oxidation reaction of acrolein, energy required for condensation and re-gasification of acrolein is able to be reduced, resulting in efficient production of acrylic acid.

However, in the case where the pressure in the condenser is adjusted lower than atmospheric pressure, when the purified gas is introduced into the second reactor without the pressure of the purified gas being raised, the purified gas does not possibly pass through the second reactor sufficiently due to pressure loss in the second reactor. Otherwise, an outlet pressure of the second reactor needs to be highly reduced in order that the purified gas passes through the second reactor sufficiently, that causes increase in equipment cost. Therefore, the purified gas obtained by the partial-condensation step is preferably introduced into the second reactor at a pressure Ps higher than a pressure Pc, the pressure in the condenser. In the case where the pressure Pc is lower than atmospheric pressure, by introducing the purified gas into the second reactor at the pressure Ps higher than the pressure Pc, the purified gas is allowed to easily pass through the second reactor, that enables efficient production of acrylic acid at low cost.

The inlet pressure Ps of the second reactor is preferably adjusted to be higher than atmospheric pressure. When the inlet pressure Ps of the second reactor is higher than atmospheric pressure, the purified gas is allowed to easily pass through the second reactor even though, for example, the outlet pressure of the second reactor is adjusted to be lower than atmospheric pressure (that is, the outlet side of the second reactor is not decompressed). The inlet pressure Ps of the second reactor is preferably 110 kPa or higher, and more preferably 120 kPa or higher. The upper limit of the inlet pressure Ps of the second reactor is not particularly limited; however, when the pressure Ps is excess high, acrolein contained in the purified gas easily condenses, resulting in increase in equipment cost for a pressure riser; and therefore, the pressure Ps is preferably 300 kPa or lower, more preferably 250 kPa or lower, and even more preferably 200 kPa or lower.

A pressure riser may be employed for raising the pressure of the purified gas from the pressure Pc to the pressure Ps in introducing the purified gas from the condenser to the second reactor. No particular limitation is placed on the pressure riser, as long as the pressure riser has an inlet port, which indraws the purified gas discharged from the condenser, and an outlet port, which exhausts the indrawn purified gas, and the inlet side is decompressed and the pressure in the outlet side is raised from the inlet side.

As the pressure riser, an apparatus which compressed the purified gas and discharges the pressured purified gas from the outlet thereof is shown, for example. As such pressure riser, a blower or a compressor may be used. The blower preferably has a compression ratio of 1.1 or higher and lower than 2.0, and the compressor preferably has a compression ratio of 2.0 or higher.

As the blower and the compressor, a positive displacement type such as a reciprocating type (including a piston ring type, a labyrinth piston type and a plunger type), a rotary type, a root type, a rolling piston type, a screw type, a swash plate type, a diaphragm type, a scroll type and a rotary vane type; a dynamic type such as a centrifugal type, an axial-flow type and a diagonal-flow type; and others can be employed; and a positive displacement type blower or compressor is preferably employed. When a positive displacement type blower or compressor is used, the inlet side is easily decompressed. In addition, the purified gas is able to be highly-compressed from low pressure to high pressure in raising pressure of the purified gas from the pressure Pc to the pressure Ps. Among them, a root type or diaphragm type blower or compressor is preferably employed, from a viewpoint of easily preventing impurities being mixed into the purified gas, that is attributed to the blower or compressor; and more preferably, a root blower or compressor is employed, in consideration of possibility of handling larger amount of the purified gas, stably transferring the purified gas while suppressing pulsation, and easily maintenance and inspection.

Regarding the pressure riser, an outlet pressure of the pressure riser may be increased by introducing the purified gas into the pressure riser along with an adjustment gas. In this case, total pressure of a discharged gas from the pressure riser may be adjusted at the pressure Ps. The venturi effect is preferably utilized for adding the adjustment gas to the purified gas in the pressure riser. In this case, it is preferred that the pressure riser has an introducing path for the adjustment gas, wherein a part of the introducing path is narrowed and a suction port for the purified gas is provided at the narrowed part. And, it is preferred that velocity of the adjustment gas is increased at the narrowed part of the introducing path by feeding the adjustment gas to the pressure riser through the introducing path at high pressure, thereby joining the purified gas with the adjustment gas. By joining the purified gas with the adjustment gas in this manner, pressure in the outlet side of the pressure riser is able to be increased from that in the inlet side (the inlet side for the purified gas). Such apparatus is available commercially as an ejector.

As the adjustment gas which is introduced into the pressure riser, a gas inactive to the oxidation reaction of acrolein is preferably used, in consideration of the latter acrolein oxidation step. Or, it is also preferable that an oxygen (molecular oxygen)-containing gas is used as an oxidant for the oxidation reaction of acrolein. Further, at least a part of offgas generated after collecting acrylic acid from an acrylic acid-containing gas obtained by the latter acrolein oxidation step may be used as the adjustment gas.

In the case of introducing the adjustment gas into the pressure riser, a fan or a blower may be provided at the outlet of the pressure riser and velocity of the purified gas at the outlet of the pressure riser may be ensured. The fan preferably has a compression ratio of lower than 1.1. The fan or blower provided at the outlet of the pressure riser, that is suitable for transferring the purified gas, is preferably selected, and the fan or blower of dynamic type such as a centrifugal type, an axial-flow type and a diagonal-flow type is preferably employed.

A plurality of the pressure risers may be provided in tandem. For example, in the case where single pressure riser does not provide sufficient capability of decompressing the inlet side of the pressure riser to a demanded pressure or compressing the purified gas at the outlet side of the pressure riser to a demanded pressure, multistage pressure risers may be employed in combination.

When the pressure of the purified gas is raised by the pressure riser, a part of acrolein contained in the purified gas is allowed to easily liquefy (condense). Therefore, a heating means is preferably provided before or after the pressure riser to heat the purified gas for suppressing liquefaction of acrolein. Thus, it is preferred that the purified gas discharged from the condenser is heated and then introduced into the pressure riser, or introduced into the pressure riser to be compressed and then heated. In the latter case, the pressure of the purified gas after heating may be adjusted at the pressure Ps. In respect of suppressing liquefaction of acrolein more effectively, the purified gas is preferably introduced into the pressure riser after heating.

In the case where the adjustment gas is introduced into the pressure riser to increase the pressure of the purified gas, it is also preferred that the high-temperature adjustment gas is introduced into the pressure riser to raise the temperature of the purified gas. In this case, temperature of the adjustment gas needs to be higher than that of the purified gas to introduced into the pressure riser.

The purified gas which pressure is raised by the pressure riser from the pressure Pc to the pressure Ps is introduced into the second reactor for conducting oxidation reaction of acrolein to obtain the acrylic acid-containing gas. By regulating the purified gas in this manner, acrylic acid is able to be efficiently produced while suppressing polymerization of acrolein.

Regarding the acrolein oxidation step, conditions in oxidation reaction of acrolein and others are explained in detail. A conventionally-known catalyst may be used as the acrolein oxidation catalyst, and examples of the catalyst include, for example, metal oxides such as iron oxide, molybdenum oxide, titanium oxide, vanadium oxide, tungsten oxide, antimony oxide, tin oxide, and copper oxide; and complex oxides of these metal oxides. Among them, a molybdenum-vanadium catalyst containing molybdenum and vanadium as main components is particularly suitable. As the molybdenum-vanadium catalyst, a complex oxide catalyst indicated as follows is particularly suitable: $Mo_aV_bQ_cR_dS_eT_fO_x$ [wherein Mo is molybdenum; V is vanadium; Q represents at least one kind element selected from the group consisting tungsten and niobium; R represents at least one kind element selected from the group consisting of iron, copper, bismuth, chromium and antimony; S represents at least one kind element selected from the group consisting of alkali metals and alkali earth metals; T represents at least one kind element selected from the group consisting of silicon, aluminum and titanium; O is oxygen; a, b, c, d, e, f and x mean atomic ratios of Mo, V, Q, R, S, T and O, respectively, and meet inequalities: $a=12$, $2 \leq b \leq 14$, $0 \leq c \leq 12$, $0 \leq d \leq 6$, $0 \leq e \leq 6$ and $0 \leq f \leq 30$, respectively; and x is a numeral value determined by oxidation states of respective elements. The acrolein oxidation catalyst may be formed by supporting the above-described metal oxide or complex oxide on an inorganic carrier.

As the second reactor in which the acrolein oxidation catalyst is placed, a fixed-bed reactor, a fluidized-bed reactor, a moving-bed reactor or the like can be employed. In respect of suppressing physical damage of catalyst such as abrasion and elongating catalyst lifetime, a fixed-bed reactor is preferably employed as the second reactor.

For producing acrylic acid by oxidation of acrolein, a conventionally-known method may be employed; and it is preferred that acrolein contained in the purified gas is oxidized in a gas phase by contacting with molecular oxygen in the presence of the acrolein oxidation catalyst at temperature of 200° C. to 400° C. The molecular oxygen may be originally contained in the acrolein-containing gas obtained by the glycerin dehydration step or may be added to the purified gas in advance of the acrolein oxidation step. In the latter case, the molecular oxygen may be added to the purified gas as an oxygen-containing gas, and examples of the oxygen-containing gas include pure oxygen and air. In addition, as described above, the oxygen-containing gas may be introduced into the pressure riser as the adjustment gas to be added to the purified gas.

In the acrolein oxidation step, composition of the purified gas may be adjusted by adding a gas, which is inactive to the acrolein oxidation reaction, to the purified gas, followed by conducting oxidation reaction of acrolein. Examples of the gas inactive to the acrolein oxidation reaction include nitrogen gas, carbon dioxide and steam. The gas inactive to the acrolein oxidation reaction may be introduced into the pressure riser as the adjustment gas to be added to the purified gas, as explained above. Composition of the purified gas introduced into the second reactor is indicated as follows: 1 mol % to 15 mol % (preferably 4 mol % to 12 mol %) of acrolein, 0.5 mol % to 25 mol % (preferably 2 mol % to 20 mol %) of molecular oxygen, 0 mol % to 30 mol % (preferably 0 mol % to 25 mol %) of steam and the rest of an inactive gas such as nitrogen gas.

In the case where a fixed-bed reactor is used as the second reactor, space velocity of the purified gas introduced into the fixed-bed reactor is preferably 300 hr$^{-1}$ or more, more preferably 500 hr$^{-1}$ or more, even more preferably 1000 hr$^{-1}$ or more, and preferably 20000 hr$^{-1}$ or less, more preferably 10000 h$^{-1}$ or less, even more preferably 5000 h$^{-1}$ or less.

In the acrolein oxidation step, an acrylic acid-containing gas is obtained by oxidation of acrolein. The acrylic acid-containing gas may be cooled to condense acrylic acid, thereby obtaining a crude acrylic acid solution, or may be brought into contact with a collection solvent, thereby obtaining a crude acrylic acid solution. Thus obtained crude acrylic acid solution is preferably purified by a refining means such as distillation, diffusion or crystallization, thereby obtaining purified acrylic acid.

[Process for Producing Hydrophilic Resin]

A process for producing a hydrophilic resin of the present invention is explained. A process for producing a hydrophilic resin of the present invention comprises the step of polymerizing a monomeric component(s) including the acrylic acid obtained by the process for producing acrylic acid of the present invention. Examples of the hydrophilic resin include a water-absorbent resin and a water-soluble resin, and the process for producing a hydrophilic resin of the present invention is particularly preferably applied to production of a water-absorbent resin.

The water-absorbent resin means water-swellable and water-insoluble polyacrylic acid having a crosslinked structure, which forms water-insoluble hydrogel containing preferably 25 mass % or less, more preferably 10 mass % or less of a water-soluble component (a water-soluble fraction) by absorbing deionized water or normal saline solution in an amount of 3 times or more, preferably 10 times to 1000 times as much as weight of the polymer itself. Specific examples and measurement methods of physical properties of the water-absorbent resin like this is described in U.S. Pat. Nos. 6,107,358, 6,174,978, 6,241,928 and others.

For producing the water-absorbent resin, acrylic acid is subjected to a neutralization step, a polymerization step and a drying step to be conducted desired treatments. Further, a crosslinking step may be conducted during the polymerization or after the polymerization.

The neutralization step is optional and a conventionally-known method may be employed. For example, a method of mixing powder or aqueous solution of a certain amount of a basic substance with acrylic acid or polyacrylic acid (salt) is shown. The neutralization step may be conducted either before or after the polymerization step or both before and after the polymerization step. As the basic substance used for neutralizing acrylic acid or polyacrylic acid (salt), conventionally-known basic substances such as, for example, (hydrogen) carbonates, alkali metal hydroxides, ammonia and organic amines may be used appropriately. Neutralization ratio of the polyacrylic acid is not particularly limited and may be adjusted to be in the range of 30 mol % to 100 mol %.

In the polymerization step, acrylic acid and/or its salt is used as a main component (preferably 70 mol % or more, and more preferably 90 mol % or more) of monomeric components, and further about 0.001 mol % to 5 mol % (value relative to acrylic acid) of a crosslinking agent and about 0.001 mol % to 2 mol % (value relative to the monomeric components) of a radical polymerization initiator are used to conduct crosslinking polymerization. A polymerization method employed in the polymerization step is not particularly limited, and a conventionally-known polymerization method such as polymerization using a radical polymerization initiator (e.g. water-solution polymerization method and inverse suspension polymerization method), radiation polymerization, polymerization by radiating electron beam or active energy beam, and ultraviolet polymerization using a photosensitizer may be employed. Various conditions such as kinds of the polymerization initiator and polymerization conditions may be adopted appropriately. Further, conventionally-known additives such as other monomers, a water-soluble chain transfer agent and hydrophilic polymers may be added, if necessary.

Acrylic acid (salt) polymer obtained by the polymerization step is subjected to a drying step. A drying method is not particularly limited and a conventionally-known drying means such as a hot-air drier, a fluidized-bed drier, and a Nauta drier may be used; and drying is appropriately conducted at temperature, for example, in the range of 70° C. to 230° C.

The water-absorbent resin obtained by the drying step may be used as-is, or may be further granulated into a desired shape, pulverized or subjected to surface-crosslinking treatment. In addition, the water-absorbent resin may be subjected to post-treatments corresponding to its usage such as adding conventionally-known additives including a reducing agent, a fragrance and a binder.

[Process for Producing Acrylic Ester and Acrylic Ester Resin]

A process for producing an acrylic ester of the present invention is explained. A process for producing an acrylic ester of the present invention comprises the step of esterifying the acrylic acid obtained by the process for producing acrylic acid of the present invention. An esterification reaction only needs to cause dehydrating condensation reaction of carboxylic group of acrylic acid and hydroxyl group of alcohol, and preferably conducted in the presence of a catalyst. For producing acrylic ester, a method disclosed in Japanese Examined Patent Application Publication No. H06-86406 may be adopted.

As an esterification catalyst, a strongly acidic cation-exchange resin may be used, for example. As the strongly acidic cation-exchange resin, C-26C (available from Duolite Company), PK-208, PK-216, PK-228 (respectively available from Mitsubishi Chemical Corporation), MSC-1,88 (available from The Dow Chemical Company), amberlist-16 (available from Rohm and Haas Company), SPC-108, SPC-112 (respectively available from Bayer AG) and others are shown. As the alcohol, a short-chain aliphatic alcohol having carbon number of 1 to 4 or an alicyclic alcohol may be used, for example.

The esterification reaction is usually performed in a liquid phase, and the reaction temperature is generally in the range of 50° C. to 110° C. though it varies depend on kinds of the reaction. In the esterification reaction, the above-described polymerization inhibitor may be used.

Next, a process for producing an acrylic ester resin of the present invention is explained. A process for producing an acrylic ester resin of the present invention comprises the step of polymerizing a monomeric component(s) including the acrylic ester obtained by the producing process of the present invention. The acrylic resin is able to be prepared by polymerizing the acrylic ester by using a known polymerization method. Further, polymerization may be conducted by using (meth)acrylic acid, its ester or an amide in combination, thereby obtaining a desired polymer. As the polymerization method, a known polymerization method such as solution polymerization, suspension polymerization, emulsion polymerization and bulk polymerization can be used. As with general (meth)acrylate polymer, a polymer having various properties is able to be obtained by designing based on the FOX, equation using a glass-transition temperature of homopolymer of each monomeric component as a indicator. The obtained acrylic ester resin is able to be utilized for various application such as adhesives, dispersants, bonds, films, sheets and paints.

This application claims priority to Japanese Patent Application No. 2011-215651, filed on Sep. 29, 2011, and Japanese Patent Application No. 2011-280519, filed on Dec. 21, 2011, and the entire contents of which are incorporated by reference herein.

EXAMPLES

The present invention is hereinafter described more specifically by reference to Examples; however, the present invention is not limited to these Examples, and can be put into practice after appropriate modifications or variations within a range meeting the gist of the present invention, all of which are included in the technical scope of the present invention.

(1) Preparation of a Catalyst (1-1) Preparation of a Glycerin Dehydration Catalyst 300 g of boric acid (available from Tomiyama Pure Chemical Industries), 673 g of diammonium hydrogenphosphate (available from Nippon Chemical Industries) and 41 g of sodium nitrate (available from Wako Pure Chemical Industries) were fed to a kneader of 1.5 L volume in sequence and mixed for 1.5 hours. Then, thus obtained mixture was dried under air-flowing at 120° C. for 12 hours and further heated under air-flowing at 450° C. for 10 hours for the purpose of decomposing and removing nitrogen components which was assumed to exist in the mixture to give a solid matter. The obtained solid matter is calcinated under air-flowing at 1000° C. for 5 hours. Thus obtained calcinated product was pulverized by a hammer mill to a powdery matter. The above operations were repeatedly conducted to obtain about 8 kg of the powdery matter. This powdery matter was treated as a compact precursor.

500 g of the compact precursor was fed to a kneader of 1.5 L volume and 70 g of deionized water was added thereto in several parts while mixing, thereby obtaining a wetting matter. The obtained wetting matter was molded by a twin-screw extruder into a ring shape having 6 mm of outer diameter, 2 mm of inner diameter and 6 mm of length. Thus obtained compact was placed in a dryer and dried under air-flowing at 120° C. for 12 hours. Then, the dried matter was calcinated under air-flowing at 700° C. for 5 hours, and the obtained calcinated matter was treated as a molded catalyst. The above operations were repeatedly conducted to obtain about 5 kg of the molded catalyst. Thus obtained molded catalyst was a glycerin dehydration catalyst comprising boron phosphate to which sodium was added and having a ring shape.

(1-2) Preparation of an Acrolein Oxidation Catalyst

Into 2500 mL of water which was stirred while heating, 350 g of ammonium paramolybdate, 116 g of ammonium metavanadate, and 44.6 g of ammonium paratungstate were dissolved, and then, 1.5 g of vanadium trioxide was further added thereto. Separately, into 750 mL of water which was stirred while heating, 87.8 g of copper nitrate was dissolved, and then, 1.2 g of copper (1) oxide and 29 g of antimony trioxide were added thereto. Thus obtained two solutions were mixed, 1000 mL of spherical α-alumina having a diameter of 3 mm to 5 mm as a carrier was fed thereto, and then, the resultant mixture was evaporated to dryness while mixing to obtain a catalyst precursor. The catalyst precursor was calcinated at 400° C. for 6 hours to give an acrolein oxidation catalyst.

(2) Study on Effect of Adding a Polymerization Inhibitor (2-1) Production Example 1

Figure 2:
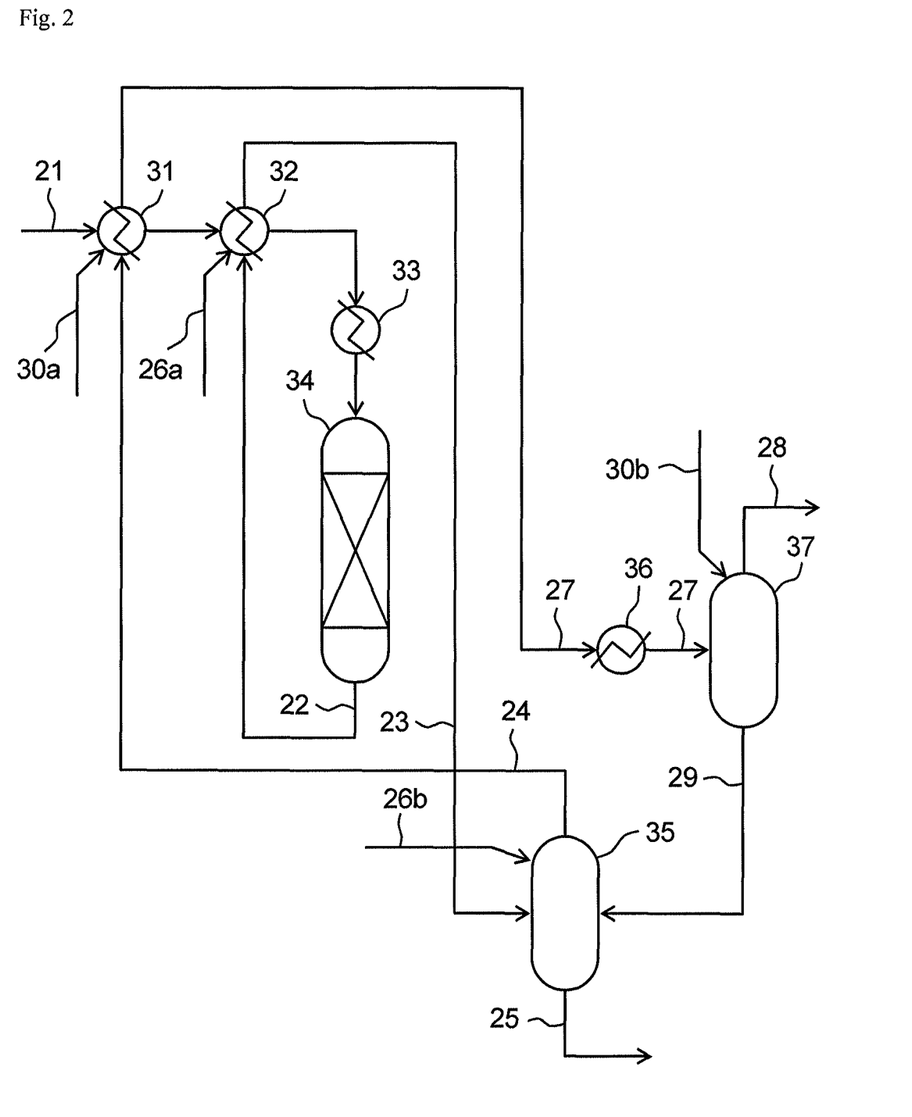
FIG. 2 shows a flow diagram of a process for producing acrolein used in Examples 1 to 4.

Acrolein was produced, using production facilities shown in FIG. 2. 5.70 kg/h of 80 mass % glycerin aqueous solution, a raw material 21, was introduced into heat exchangers 31, 32, 33 sequentially along with 2.0 kg/h of nitrogen gas, a carrier gas, and heated to 360° C. to give a glycerin-containing gas. This gas was fed to a fixed-bed reactor 34 (3 cm of an inner diameter of a reaction tube, 2.0 m of catalyst layer length, 5 reaction tubes, 1.3 L of the above-prepared molded catalyst filled in the one reaction tube) which was kept at 360° C. by a molten salt bath, at a pressure of 101 kPa. From the reactor 34, an acrolein-containing gas 22 comprising 40.5 mass % of acrolein, 48.7 mass % of water, 10.8 mass % of hydroxyacetone was obtained. The acrolein-containing gas 22 was introduced into the heat exchanger 32, a condenser, to heat the raw material 21, whereby the acrolein-containing gas 22 was cooled to 85° C. As a result, a part of acrolein, water and hydroxyacetone, a high-boiling substance, contained in the acrolein-containing gas 22 condensed to give a gas-liquid mixture 23. At this time, 0.012 kg/h of 4 mass % hydroquinone aqueous solution, a polymerization inhibitor 26a, was added to the heat exchanger 32 on the side of a line 22-23 (that was a line in which the acrolein-containing gas 22 or the gas-liquid mixture 23 flew). The gas-liquid mixture 23 was introduced into a gas-liquid separator 35 to be separated into a purified gas 24 and a condensate 25. The separated purified gas 24 was introduced into the heat exchanger 31, a condenser, to heat the raw material 21, whereby the purified gas 24 was cooled to 80° C., and sequentially introduced into a heat exchanger 36, a condenser, to be cooled to 50° C. As a result, a part of acrolein, water and hydroxyacetone, a high-boiling substance, contained in the purified gas 24 condensed to give a gas-liquid mixture 27. At this time, 0.010 kg/h of 4 mass % hydroquinone aqueous solution 26a, a polymerization inhibitor 30a, was added to the heat exchanger 31 on the side of a line 24-27 (that was a line in which the purified gas 24 or the gas-liquid mixture 27 flew). The gas-liquid mixture 27 was introduced into a gas-liquid separator 37 to be separated into a second purified gas 28 and a second condensate 29. The second purified gas 28 contained 89.0 mass % of acrolein, 10.7 mass % of water and 0.3 mass % of hydroxyacetone and was produced at 2.53 kg/h and recovered as purified acrolein. The second condensate 29 was returned to the gas-liquid separator 35 and the condensate 25 discharged from the gas-liquid separator 35 was separated as a waste liquid. The condensate 25 was generated at 3.19 kg/h and contained 79.2 mass % of water, 19.1 mass % of hydroxyacetone, 1.7 mass % of acrolein and 0.03 mass % of hydroquinone.

In the production example 1, liquid phases of the gas-liquid mixture 23 and the gas-liquid mixture 27 formed single liquid phase and the second condensate also formed single liquid phase. Troubles such as blockage in pipes due to acrolein polymerization was not observed and operation of the facility was stably conducted for a long period.

(2-2) Production Example 2

Acrolein was produced in the same manner as in the production example 1, except that 0.078 kg/h of 4 mass % hydroquinone aqueous solution was added to the heat exchanger 31 on the side of the line 24-27 as a polymerization inhibitor 30a, and the purified gas 24 was cooled to 25° C. at the heat exchanger 31 and then heated to 50° C. at the heat exchanger 36. As a result, the second purified gas 28 (namely, purified acrolein) containing 89.0 mass % of acrolein, 10.7 mass % of water and 0.2 mass % of hydroxyacetone was produced at 2.53 kg/h, and the condensate 25 (namely, a waste liquid) containing 79.5 mass % of water, 18.7 mass % of hydroxyacetone, 1.7 mass % of acrolein and 0.11 mass % of hydroquinone was obtained at 3.26 kg/h.

In the production example 2, liquid phase of the gas-liquid mixture 27 was separated into two phases. In the production example 2, troubles such as blockage in pipes due to acrolein polymerization was not observed and operation of the facility was stably conducted for a long period; however, turbidness due to white deposit was observed in the condensate 25 (a waste liquid) and formation of white deposit in the liquid phase of the gas-liquid mixture 27 was recognized.

(2-3) Production Example 3

Acrolein was produced in the same manner as in the production example 1, except that 4 mass % hydroquinone aqueous solution was added to the gas-liquid separator 35 as a polymerization inhibitor 26b instead of adding the polymerization inhibitor 26a to the heat exchanger 32 on the side of the line 22-23, and 4 mass % hydroquinone aqueous solution was added to the gas-liquid separator 37 as a polymerization inhibitor 30b instead of adding the polymerization inhibitor 30a to the heat exchanger 31 on the side of the line 24-27.

In the production example 3, three days after the start of operation, blockage due to formation of acrolein polymerization occurred inside the heat exchanger 32 on the side of the line 22-23, in the flow path of the gas-liquid mixture 23, inside the heat exchanger 31 on the side of the line 24-27, and in the flow path of the gas-liquid mixture 27, and hence, continuous operation of the facilities was stopped.

(2-4) Production Example 4

Acrolein was produced in the same manner as in the production example 2, except that the polymerization inhibitor 26a and the polymerization inhibitor 30a were not added. In the production example 4, half-day after the start of operation, blockage due to formation of acrolein polymerization occurred inside the heat exchanger 32 on the side of the line 22-23, in the flow path of the gas-liquid mixture 23, inside the heat exchanger 31 on the side of the line 24-27, and in the flow path of the gas-liquid mixture 27, and hence, continuous operation of the facilities was stopped.

(3) Study on Effect of Pressure Adjustment of a Purified Gas (3-1) Production Example 5

Figure 3:
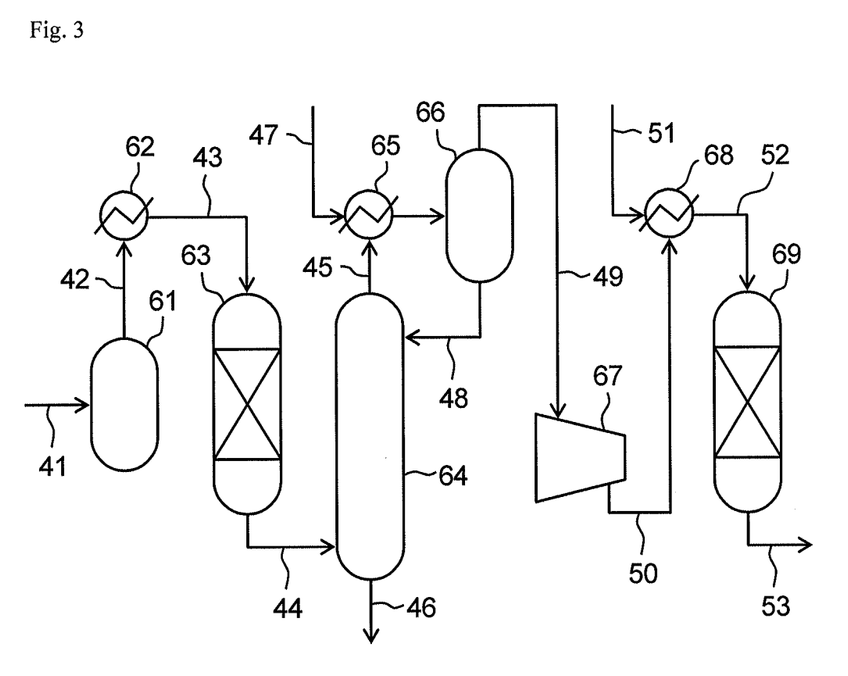
FIG. 3 shows a flow diagram of a process for producing acrylic acid used in Example 5.

Acrylic acid was produced from glycerin, using production facilities shown in FIG. 3. The production facilities shown in FIG. 3 comprised an evaporator 61 for evaporating glycerin aqueous solution, a first reactor 63 for conducting dehydration reaction of glycerin, a condenser 65 for condensing a high-boiling substance contained in the acrolein-containing gas which was obtained from the first reactor 63, a pressure riser 67 for raising the pressure of the acrolein-containing gas discharged from the condenser 65, and a second reactor 69 for conducting oxidation reaction of acrolein contained in the acrolein-containing gas. In the production facilities shown in FIG. 3, the pressure riser 67 created decompressed atmosphere between from the evaporator 61 to the inlet of the pressure riser 67. In the below explanation, a component contained less than 1 mass % was omitted.

13.9 kg/h of glycerin aqueous solution (comprising 80.8 mass % of glycerin, 16.5 mass % of water, 0.8 mass % of inorganic salts and 1.9 mass % of other components) derived from a vegetable oil was fed to a thin-film evaporator retained under a pressure of 10 kPa to obtain 13.4 kg/h of a distillate (comprising 82.3 mass % of glycerin, 17.1 mass % of water, 0.1 mass % of inorganic salts and 0.4 mass % of other components). Into the obtained distillate, 0.5 kg/h of water was added, thereby obtaining 13.8 kg/h of purified glycerin aqueous solution (comprising 79.6 mass % of glycerin, 19.9 mass % of water, 0.1 mass % of inorganic salts and 0.4 mass % of other components).

The purified glycerin aqueous solution 41 was fed to the evaporator 61 to gasify, thereby giving a glycerin-containing gas 42. The glycerin-containing gas 42 was introduced into a heat riser 62 (a heat exchanger) to be heated to 360° C., followed by introducing into a first reactor 63, a fixed-bed reactor, at 13.8 kg/h. The first reactor 63 was filled with a glycerin dehydration catalyst and kept at 360° C. by a molten salt bath. Composition of the glycerin-containing gas 43 introduced into the first reactor 63 comprised 80 mass % of glycerin and 20 mass % of water, and space velocity (SV) of that was 390 hr$^{-1}$. In the first reactor 63, glycerin contained in the glycerin-containing gas 43 was dehydrated, thereby obtaining an acrolein-containing gas 44 containing 39 mass % of acrolein, 10 mass % of hydroxyacetone and 50 mass % of water at 13.8 kg/h. At this time, an inlet pressure of the first reactor 63 was 52 kPa and an outlet pressure of that was 42 kPa.

The acrolein-containing gas 44 discharged from the first reactor 63 was introduced into an absorption column 64 (number of theoretical stages was 4) from the lower part thereof, cooled by an absorbing liquid to condense a part of a high-boiling substance, and then discharged from the top of the column at 15.7 kg/h. An acrolein-containing gas 45 discharged from the top of the absorption column 64 had a composition of 36 mass % of acrolein and 64 mass % of water, and had temperature of 68° C. An outlet pressure of the absorption column 64 (that is, pressure of the acrolein-containing gas 45 discharged from the absorption column 64) was 34 kPa. The acrolein-containing gas 45 discharged from the absorption column 64 was introduced into a condenser 65 (a heat exchanger), cooled to 54° C. to condense a part of a high-boiling substance, and then introduced into a gas-liquid separator 66 to be separated into a condensate 48 and a purified gas 49, which at least a part of the high-boiling substance had been removed. Into the condenser 65, hydroquinone aqueous solution 47 (comprising 5 mass % of hydroquinone and 95 mass % of water) of a polymerization inhibitor was fed at 0.1 kg/h. Ratio of acrolein condensed in the condenser 65 was 5 mass %. In the gas-liquid separator 66, the condensate 48 (comprising 3 mass % of acrolein and 97 mass % of water) was obtained at 9.1 kg/h, and the condensate 48 was fed to the absorption column 64 from the top thereof to be utilized as the absorbing liquid. A waste liquid 46 (comprising 1 mass % of acrolein, 20 mass % of hydroxyacetone and 79 mass % of water) was extracted from the bottom of the absorption column 64 at 7.1 kg/h.

The purified gas 49 separated as a gas phase by the gas-liquid separator 66 had pressure of 34 kPa and temperature of 54° C., and introduced into a pressure riser 67, thereby raising the pressure to 150 kPa and heating to 160° C. A purified gas 50 discharged from the pressure riser 67 was incorporated with a composition adjustment gas 51, and introduced into a heat riser 68 (a heat exchanger) to be heated to 260° C., followed by introducing into a second reactor 69, a fixed-bed reactor, at 54.5 kg/h. Composition of a purified gas 52 introduced into the second reactor 69 comprised 10 mass % of acrolein, 6 mass % of water, 5 mass % of oxygen and 79 mass % of nitrogen gas, and space velocity (SV) of that was 1550 hr$^{-1}$. An inlet pressure of the second reactor 69 was 150 kPa. The second reactor 69 was filled with an acrolein oxidation catalyst and kept at 360° C. by a molten salt bath. In the second reactor 69, acrolein contained in the purified gas 52 was oxidized, thereby obtaining an acrylic acid-containing gas 53.

The acrylic acid-containing gas 53 discharged from the second reactor 69 was introduced into a condenser, which was cooled by cooling water of about 15° C., to be cooled and condensed, and further introduced into a receiver, which was cooled by an ice bath, and a subsequently-installed cold trap to be recovered. Mass of the recovered acrylic acid-containing composition was 10.2 kg/h, that was 98 mass % of the theoretical yield. The acrylic acid-containing composition was quantitatively analyzed by gas chromatograph and found that it contained 65 mass % of acrylic acid and 35 mass % of water. Yield of acrylic acid based on the purified glycerin fed to the first reactor was 76%.

(3-2) Production Example 6

Figure 4:
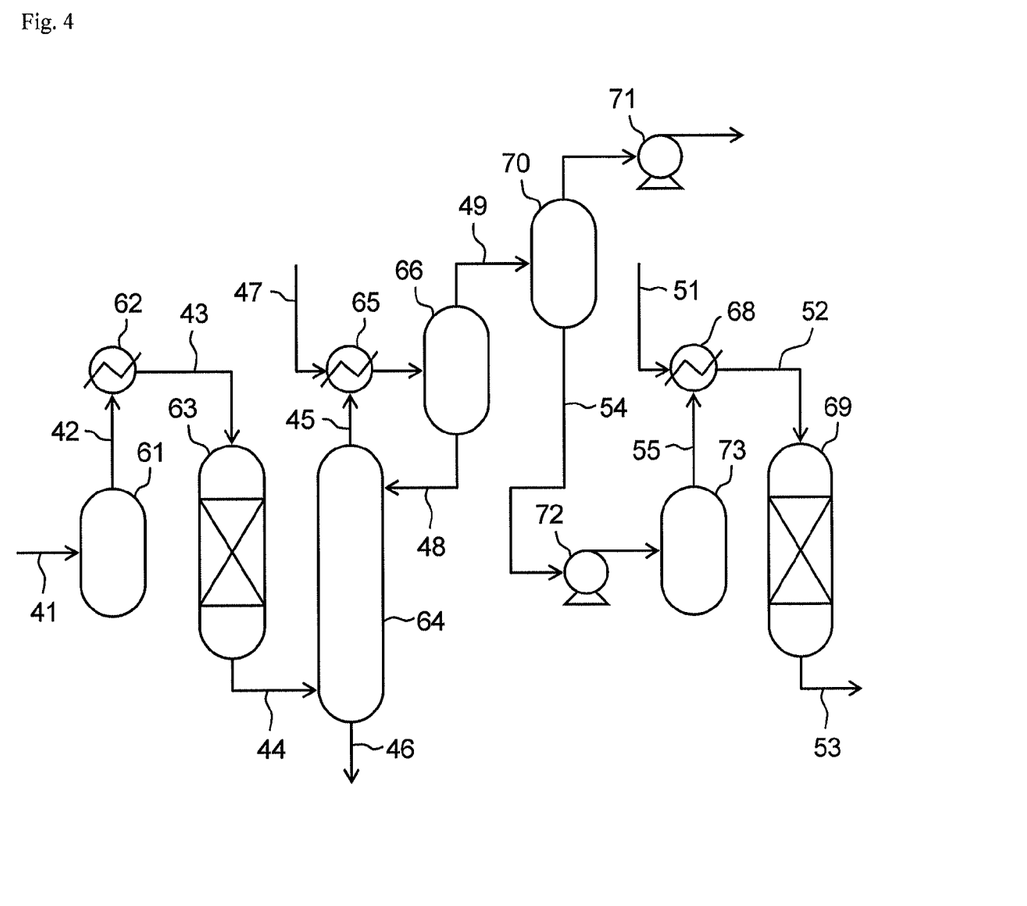
FIG. 4 shows a flow diagram of a process for producing acrylic acid used in Example 6.

Acrylic acid was produced from glycerin, using production facilities shown in FIG. 4. The production facilities shown in FIG. 4 was the same as the production facilities shown in FIG. 3, except that a vacuum pump 71 was installed instead of the pressure riser 67 and a condenser 70 for condensing and recovering acrolein, a pump 72 for transferring condensed acrolein, and an evaporator 73 for evaporating condensed acrolein were provided. In the production facilities shown in FIG. 4, an outlet side of the vacuum pump 71 was open to the atmosphere and the vacuum pump 71 created decompressed atmosphere between from the evaporator 61 to the condenser 70. In the below explanation, a component contained less than 1 mass % was omitted.

The same operations were performed until the condensate 48 and the purified gas 49, which at least a part of a high-boiling substance had been removed, were separated from each other by the gas-liquid separator 66. The purified gas 49 separated as a gas phase by the gas-liquid separator 66 had pressure of 34 kPa and temperature of 54° C. This gas was introduced into a condenser 70 to be cooled and condensed, thereby obtaining an acrolein-containing solution 54 (comprising 80 mass % of acrolein and 20 mass % of water) at 6.6 kg/h. Ratio of acrolein condensed in the condenser 70 was 98 mass %.

The obtained acrolein-containing solution 54 was supplied to an evaporator 73 by a liquid transfer pump 72 and gasified, thereby obtaining an acrolein-containing gas 55 (comprising 79 mass % of acrolein and 21 mass % of water) at 6.4 kg/h. On this occasion, white powder, which seemed to be an acrolein polymer, was recognized on the bottom of the evaporator 73, and the acrolein-containing gas 55 which was re-gasified by the evaporator 73 had lost 4 mass % of acrolein from the point of cooling at the condenser 70. The acrolein-containing gas 55 re-gasified by the evaporator 73 was incorporated with 45.2 kg/h of a composition adjustment gas 51 (comprising 4 mass % of water, 6 mass % of oxygen and 90 mass % of nitrogen gas) and introduced into the heat riser 68 (a heat exchanger) to be heated to 260° C., followed by introducing into the second reactor 69, a fixed-bed reactor, at 51.6 kg/h. Composition of the acrolein-containing gas 52 introduced into the second reactor 69 comprised 10 mass %, of acrolein, 6 mass % of water, 5 mass % of oxygen and 79 mass % of nitrogen gas, and space velocity (SV) of that was 1550 hr$^{-1}$. The inlet pressure of the second reactor 69 was 150 kPa.

The acrylic acid-containing gas 53 produced by the second reactor 69 was recovered in the same manner as in the production example 5. Mass of the recovered acrylic acid-containing composition was 9.6 kg/h, that was 98 mass % of the theoretical yield. The acrylic acid-containing composition was quantitatively analyzed by gas chromatograph and found that it contained 65 mass % of acrylic acid and 35 mass % of water. Yield of acrylic acid based on the purified glycerin fed to the first reactor was 72%.

In the production example 6, since decompression was conducted by using the vacuum pump 71 instead of the pressure riser 67, it was necessitated that acrolein contained in the acrolein-containing composition 24 which was produced by the first reactor 63 was liquefied (condensed), thereby recovering as the acrolein-containing solution 54, and then the acrolein-containing solution 54 was re-gasified. In the production example 6, acrolein was recovered as an acrolein-containing solution, in which acrolein easily polymerized, and further, the acrolein-containing solution was needed to be heated for re-gasification; and hence, an acrolein polymer was formed, resulting in lowering the yield and quality of acrylic acid. In addition, in the production example 6, extra energy for liquefaction (condensation) and re-gasification of acrolein was required, and further, equipments for performing these operations was needed and extra energy for working these equipments were also required. In other words, in the production example 5, yield of acrylic acid was increased while reducing energy required for producing acrylic acid.

(4) Production Example of Acrylic Acid Derivatives (4-1) Purification of Acrylic Acid The acrylic acid-containing composition obtained in the production example 5 was supplied at 10.0 kg/h to the fifth stage of a distillation column having 10 stages and continuously distilled under the conditions of a refluxing ratio of 1 and a distillation amount from the top of the column of 3.5 kg/h. As a result, crude acrylic acid having composition of 88.1 mass % of acrylic acid, 0.01 mass % of propionic acid, 2.3 mass % of acetic acid, 0.04 mass % of formic acid and 9.5 mass % of water was obtained at 6.5 kg/h from the bottom of the column. Crystallization operation was conducted by cooling the crude acrylic acid as a mother liquid to a temperature range of −5.8° C. to room temperature (about 15° C.) to form a crystal, keeping at the same temperature, and then, separating the crystal from the liquid by suction filtration. The separated crystal was melted, and a portion of the crystal was sampled for analysis and the rest thereof was processed by the crystallization operation, in which the rest was cooled as a mother liquid to a temperature range of 4.6° C. to room temperature (about 15° C.) to form a crystal, kept at the same temperature, and then, the crystal was separated from the liquid by suction filtration, thereby conducting a second round of the crystallization operation. According to the crystallization operations repeated two times in total, purified acrylic acid with a purity of 99.9 mass % or higher was obtained finally.

(4-2) Production of a Water-Absorbent Resin

A polymerization inhibitor was added to the obtained purified acrylic acid to obtain acrylic acid containing 60 ppm by mass of the polymerization inhibitor. Thus obtained acrylic acid was added to NaOH aqueous solution, which had been separately prepared from sodium hydroxide containing 0.2 ppm by mass of iron, under cooling condition (solution temperature 35° C.) to be neutralized at 75 mol %. The contents of iron in the acrylic acid and the water were below a detection limit, and thus, the iron content in a monomer was about 0.07 ppm by mass based on the calculated value.

Into the obtained 35 mass % sodium acrylate aqueous solution, which has a neutralization ratio of 75 mol %, 0.05 mol % (relative to the sodium acrylate aqueous solution) of polyethylene glycol diacrylate as an internal crosslinking agent was dissolved to obtain a monomeric component. 350 g of the monomeric component was fed to a cylindrical vessel with a volume of 1 L, and nitrogen was blown at 2 L/minute into the vessel for 20 minutes to expel the air. Then, an aqueous solution containing 0.12 g/mol (relative to the monomeric component) of sodium persulfate and 0.005 g/mol (relative to the monomeric component) of L-ascorbic acid were added thereto while being stirred by a stirrer to start polymerization. After the start of the polymerization, stirring was stopped and static aqueous solution polymerization was conducted. The temperature of the monomeric component reached peak polymerization temperature of 108° C. after about 15 minutes (polymerization peak time), and then, polymerization was proceeded for 30 minutes. Subsequently, the resulting polymer material was taken out of the cylindrical vessel to obtain a hydrated gel-like cross-linked polymer.

The obtained hydrated gel-like crosslinked polymer was segmented at 45° C. by a meat chopper (hole diameter 8 mm) and dried at 170° C. for 20 minutes by a hot-air drier. Further, the dried polymer (solid matter: about 95%) was pulverized by a roll mill and classified by a JIS standard sieve into those having a particle diameter of 300 μm to 600 μm, thereby obtaining a polyacrylic acid water-absorbent resin (neutralization ratio 75%).

The acrylic acid obtained by the producing process of the present invention had the comparable polymerization property to acrylic acid obtained by the process of producing acrylic acid from propylene, and the obtained hydrophilic resin was free from odor and had the same physical properties as a conventional one.

(4-3) Production of an Acrylic Ester 2 mass parts of the obtained purified acrylic acid and 3 mass parts of n-butanol were used as raw materials and an ester exchange reaction was conducted at temperature of 65° C. by using a strongly acidic cation-exchange resin as a catalyst. Thus obtained reaction solution was extracted with water, whereby unreacted acrylic acid and water generated by the reaction were removed, and then, the resultant was fed to a distillation column to obtain n-butyl acrylate with a purity of 99.8 mass % or higher from the bottom of the column. Distillated n-butanol containing n-butyl acrylate, that was obtained from the top of the column, was reused for the ester exchange reaction.

(4-4) Production of an Acrylic Aster Resin and Application to an Adhesive 3 mass parts of the obtained purified acrylic acid, 96 mass parts of n-butyl acrylate, that was an ester of the acrylic acid, and 1 mass part of 2-hydroxyethyl acrylate were solution-polymerized in a mixed solution of toluene and ethyl acetate (toluene/ethyl acetate (mass ratio)=1/1) using 0.2 mass parts of azobisisobutyronitrile as a polymerization initiator for 8 hours while refluxing, thereby obtaining an acrylic polymer solution containing 50 mass % of a non-volatile content and having 500,000 of weight-average molecular weight. 1 mass part of an isocyanate cross-linking agent ("CORONATE L-55E" of a trade name, available from Nippon Polyurethane Industries) was added to 100 mass parts of the obtained acrylic polymer solution and the resultant was stirred so as to be uniformly mixed, thereby producing an adhesive.

Thus obtained adhesive was applied onto a polyethylene terephthalate (PET) film (available from Toray Industries, 25 μm thick) so that its thickness after drying was 30 μm, and was dried at 80° C. for 5 minutes. Subsequently, a release paper (available from Sun A. Kaken Company, "K-80HS" of a trade name) was attached on the surface of the adhesive to be protected, that was then cured under atmosphere of relative humidity of 65% and temperature of 23° C. for 7 days to give an adhesive film. This adhesive film was cut to a certain size to prepare a test piece.

The obtained test piece was subjected to the following holding force test at 80° C. The test piece from which the release paper had been peeled was attached on a stainless steel plate made of SUS 304 and was pressure-bonded on the stainless steel by rolling a rubber roller of 2 kg back and forth twice under atmosphere of relative humidity of 65% and temperature of 23° C. The attaching area was 25 mm×25 mm. After leaving for 25 minutes, it was hung vertically in a holding force tester set at 80° C., left for 20 minutes, and then added a weight of 1 kg. The load of this was 1.568 N/cm². The time from the start of weighting until the test piece fell from the stainless steel plate was measured; and it was found that the test piece did not fall even after 24 hours, that indicated it had a sufficient performance as an adhesive.

INDUSTRIAL APPLICABILITY

The present invention is available for producing acrolein from glycerin, and further producing acrylic acid and its derivatives.

The invention claimed is:

1. A process for producing acrolein, comprising:
   a glycerin dehydration step of conducting dehydration reaction of glycerin to obtain an acrolein-containing gas;
   a partial-condensation step of cooling the acrolein-containing gas to condense a part of acrolein, water, and a high-boiling substance selected from the group consisting of phenol, 1-hydroxyacetone, allyl alcohol, acetal and glycerin polycondensation products, contained in the acrolein-containing gas, thereby obtaining a purified gas and a condensate; and
   a separation step of separating the purified gas from the condensate;
   wherein a polymerization inhibitor is added to the acrolein-containing gas or the condensate in the partial-condensation step, and
   the mass ratio of acrolein/(water+hydroxyacetone) in the condensate is 1/99 or more.

2. The process for producing acrolein according to claim 1, wherein the condensate forms single liquid phase.

3. The process for producing acrolein according to claim 2, wherein the mass ratio of acrolein/(water+hydroxyacetone) in the condensate is 20/80 or less.

4. The process for producing acrolein according to claim 1, wherein less than 10% of acrolein contained in the acrolein-containing gas condenses in the partial-condensation step.

5. A process for producing acrylic acid, comprising:
   an acrolein oxidation step of conducting oxidation reaction of acrolein contained in the purified gas obtained by the process according to claim 1.

6. The process for producing acrylic acid according to claim 5, wherein:
   glycerin is introduced into a first reactor to conduct the dehydration reaction in the dehydration step;
   the acrolein-containing gas discharged from the first reactor is introduced into a condenser to be cooled at a pressure Pc lower than atmospheric pressure in the partial-condensation step;
   the purified gas discharged from the condenser is introduced into a second reactor to conduct the oxidation reaction of acrolein in the acrolein oxidation step; and
   the purified gas obtained by the partial-condensation step is introduced into the second reactor while acrolein contained in the purified gas remains in a gaseous state, wherein an inlet pressure of the second reactor is adjusted at a pressure Ps higher than the pressure Pc.

7. The process for producing acrylic acid according to claim 6, wherein
   the inlet pressure of the second reactor is adjusted at the pressure Ps by introducing the purified gas discharged from the condenser into an ejector as a pressure riser, followed by introducing an adjustment gas into the ejector, or
   the inlet pressure of the second reactor is adjusted at the pressure Ps by introducing the purified gas discharged from the condenser into a blower or compressor as a pressure riser, followed by compressing in the blower or compressor.

8. The process for producing acrylic acid according to claim 7, wherein
   the inlet pressure of the second reactor is adjusted at the pressure Ps by introducing the purified gas discharged from the condenser into the ejector, followed by introducing the adjustment gas having a temperature higher than that of the purified gas introduced into the ejector, into the ejector.

9. The process for producing acrylic acid according to claim 7, wherein
   the inlet pressure of the second reactor is adjusted at the pressure Ps by heating the purified gas discharged from the condenser, introducing it into the blower or compressor and then compressing, or introducing the purified gas discharged from the condenser into the blower or compressor, compressing and then heating.

10. The process for producing acrylic acid according to claim 6, wherein
    the pressure Pc is 1 kPa or higher and 80 kPa or lower, and the pressure Ps is 110 kPa or higher and 300 kPa or lower.

11. A process for producing a hydrophilic resin, comprising the step of polymerizing the acrylic acid obtained by the process according to claim 5 with a monomeric component(s).

12. The process for producing a hydrophilic resin according to claim 11, wherein the hydrophilic resin is an absorbent resin.

13. A process for producing an acrylic ester, comprising the step of esterifying the acrylic acid obtained by the process according to claim 5.

14. A process for producing an acrylic ester resin, comprising the step of polymerizing the acrylic ester obtained by the process according to claim 13 with a monomeric component(s).

* * * * *